US00PP27604P2

(12) United States Plant Patent
Roberts

(10) Patent No.: US PP27,604 P2
(45) Date of Patent: Jan. 24, 2017

(54) MINT PLANT 'TETON MINT'

(50) Latin Name: ***Mentha* sp.**
Varietal Denomination: Teton Mint

(71) Applicant: Essex Laboratories, Inc., Napavine, WA (US)

(72) Inventor: Donald D. Roberts, Independence, OR (US)

(73) Assignee: Essex Laboratories, LLC, Chehalis, WA (US)

( * ) Notice: Subject to any disclaimer, the term of this patent is extended or adjusted under 35 U.S.C. 154(b) by 0 days.

(21) Appl. No.: 14/999,511

(22) Filed: May 18, 2016

(51) Int. Cl.
*A01H 5/12* (2006.01)

(52) U.S. Cl.
USPC ..... Plt./259

(58) Field of Classification Search
USPC ..... Plt./259
See application file for complete search history.

(56) References Cited

PUBLICATIONS

Gobert, V., "Hybridization in the section *Mentha* (Lamiaceae) inferred from AFLP markers," Am. J. Bot., Dec. 2002, 89 (12), pp. 2017-2023.

Fuchs, Sabine, et al., "Biosynthesis of menthofuran in *Mentha* × *piperita* ; Stereoselective and Mechanistic Studies;" J. Agric. Food Chem., 1999, 47(10), pp. 4100-4105.

Dung, Jeremiah K. S., et al., "Evaluation of Verticillium wilt resistance in *Mentha arvensis* and *M. longifolia* genotypes," Plant Disease, Oct. 2010, vol. 94, pp. 1255-1260.

Rohloff, Jens, et al., "Effect of harvest time and drying method on biomass production, essential oil yield, and quality of peppermint (*Mentha piperita* L.);" J. Agric. Food Chem., 2005, 53(10), pp. 4143-4148.

Rohloff, Jens, "Monoterpene composition of essential oil from peppermint (*Mentha piperita* L.) with regard to leaf positions using solid-phase microextraction and gas chromatography/mass spectrometry analysis;" J. Agric. Food Chem., 1999, 47(9), pp. 3782-3786.

Padalia, Rajendra C., et al., "Essential oil composition of sixteen elite cultivars of *Mentha* from western Himalayan region, India," Maejo Int. J. Sci. Technol., 2013, 7(01), pp. 83-93.

Tsai, Mei-Lin, et al., "Chemical composition and biological properties of essential oils of two mint species," Trop. J. Pharm. Research, Aug. 2013, 12(4), pp. 577-582.

*Primary Examiner* — Annette Para
(74) *Attorney, Agent, or Firm* — Marger Johnson

(57) ABSTRACT

Mint selection 14-27-89, denominated 'Teton Mint', is a new *Mentha* sp. cultivar that produces an essential oil different in composition than commercially grown mint varieties. The essential oil is similar to standard mint oil in components composition but differs in the typical *Mentha piperita* peppermint oil.

2 Drawing Sheets

Latin name of the genus and species: *Mentha* sp.
Variety denomination: 'TETON MINT'.

FEDERAL SPONSORSHIP

None

TYPE OF PLANT AND NAME OF VARIETY

The present invention relates to a new and distinct variety of peppermint plant developed from a parent of the species *M. arvensis*. The new variety will be identified as 'Teton Mint'.

BACKGROUND OF INVENTION

'Teton Mint' originated as a seedling from an open pollinated *Mentha arvensis* female parent (08-A20-4) included with other *M. arvensis* and male fertile *M. piperita* plants in a polycross breeding program. Commercial *M. piperita* is sterile and only becomes fertile in the polyploidy state. The parent plants in the polycross breeding syscm were composed of selected fertile male and female genotypes based on certain desirable characteristics.

DISCOVERY AND ASEXUAL REPRODUCTION

This new mint was developed in a mint breeding program in which the primary objective was to develop a mint variety having a specific oil composition, acceptable yield and resistant to mint diseases. The new variety is more resistant to mint wilt (soil-borne fungus *Verticillium dahlia*) than its parent, but more susceptible to mint rust (air-borne fungus *Puccinia menthae*). Selection 'Teton Mint' has a higher yield of oil than the control variety, Black Mitcham, in test plots since 2014. This plant was selected from a population of mint seedlings in research plots on land near Monmouth, Oreg., and initially identified as 14-27-89.

'Teton Mint' is asexually propagated to maintain the cultivar's genetic integrity and as a means of increasing the selection for commercial planting. Asexual propagation, by tip cuttings or stolon sections, is a common practice in commercial mint cultivation and serves as a means of propagating the normally sterile mint plant. Under the inventor's direction, Premier Botanicals has conducted asexual propagation of 'Teton Mint' for greenhouse and field planting in Monmouth, Oreg., each year since 2014 and the genotype comes true to form with each generation.

SUMMARY OF THE INVENTION

Mint selection 14-27-89, denominated 'Teton Mint', is a new *Mentha* sp. cultivar that produces an essential oil different in composition than commercially grown mint varieties. The essential oil is similar to standard mint oil in components composition but differs in the typical ratio of components. Organo-leptically it differs from typical *Mentha piperita* peppermint oil.

BRIEF DESCRIPTION OF THE FIGURES

The accompanying color Figures show typical, field grown vegetative growth of 'Teton Mint' and depicts the color as nearly as reasonably possible.

FIG. 2 also illustrates the variance in leaf shape of my new mint plant depending on the location on plant.

DESCRIPTION OF PLANT

Figure 1:
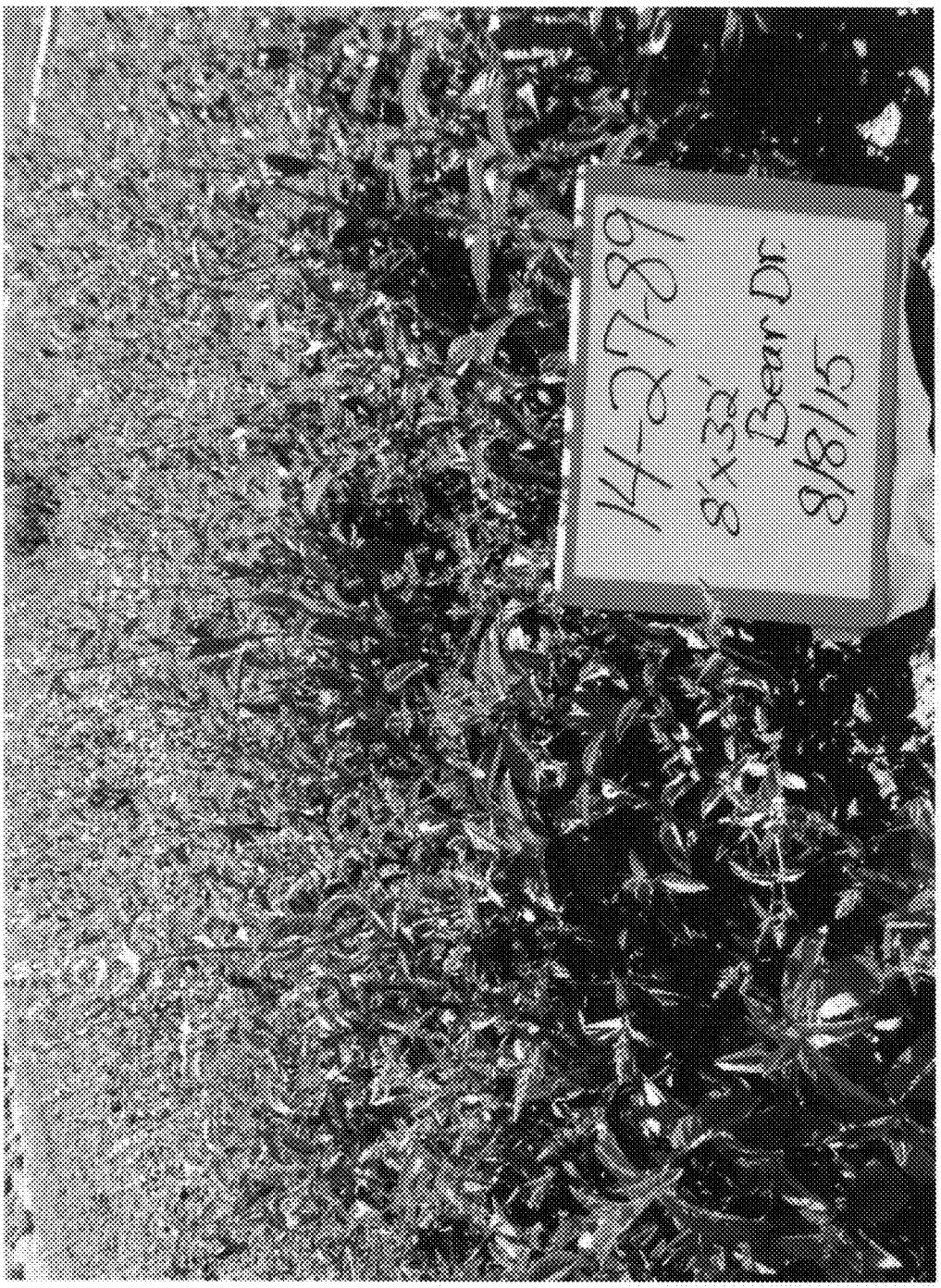
FIG. 1 illustrates the growth pattern under field management of my new mint plant in accordance with the present invention.
Figure 2:
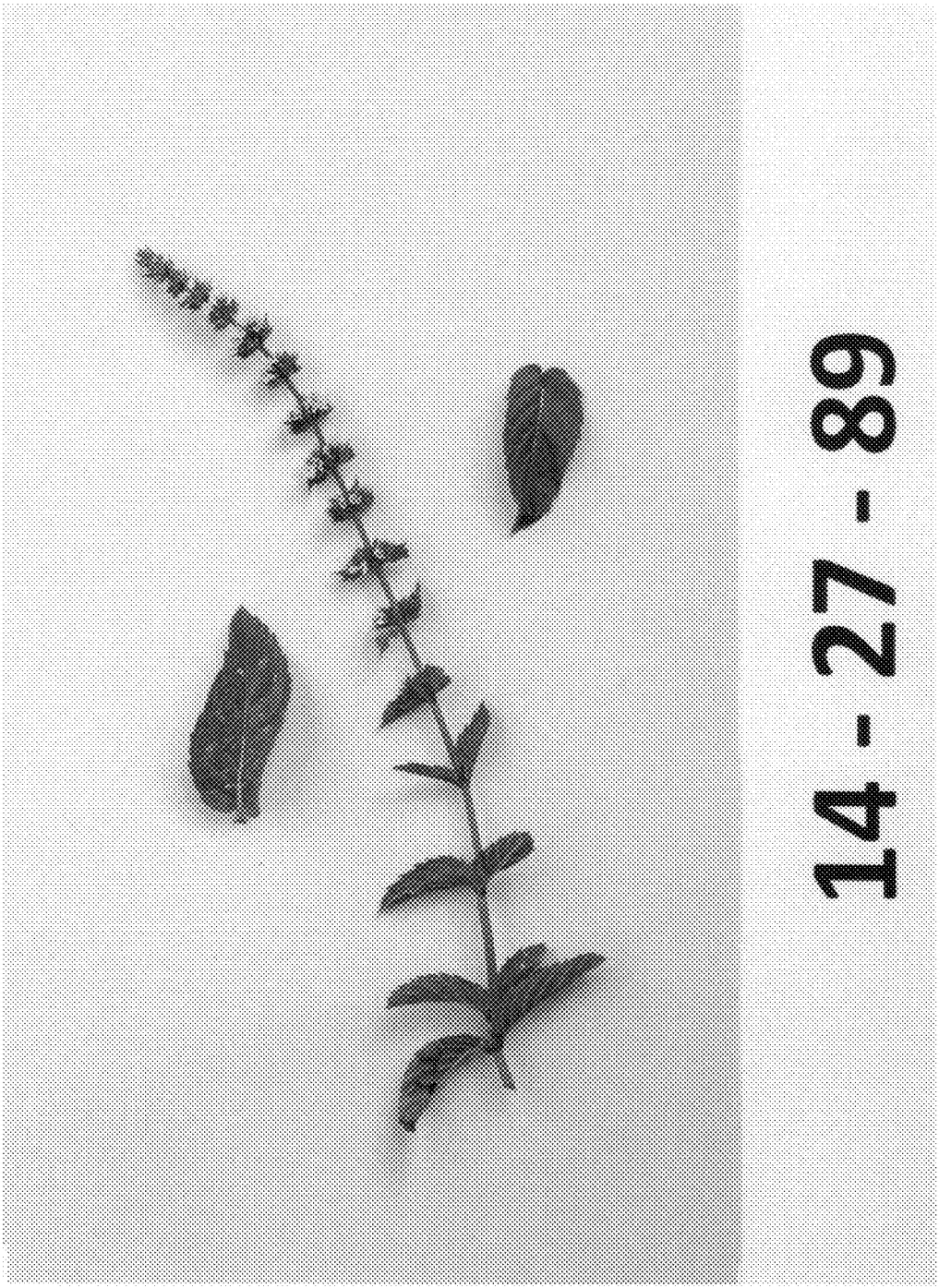
FIG. 2 illustrates the flower spike with capitate flower development at the nodes of the spike.

My new mint plant improves upon and is distinct from other mint plants in several characteristics, including but not limited to, the following:

1. The ability to produce an essential oil different in composition than typical commercial *M. arvensis*, but with similar components as 'Black Mitcham' peppermint (*M. piperita*);
2. Produce more oil on a dry weight basis than currently grown mint varieties;
3. An early spring growth similar to 'Black Mitcham' peppermint but with an earlier maturity for desirable chemical composition of its essential oil;
4. A level of resistance to mint wilt equal to or greater than that of its *M. arvensis* female parent;

The essential oil extracted from 'Teton Mint' has a composition of components more like that of commercial oil produced by 'Black Mitcham' peppermint (*M. piperita*) than that of its *M. arvensis* parent as illustrated in Table 1. However, the ratio of oil components in 'Teton Mint' is different from those of both *M. arvensis* and *M. piperita*. The concentration of menthone in oil of 'Teton Mint' is greater than that of *M. arvensis* and *M. piperita*. There is only a trace of menthofuran in the oil of 'Teton Mint' and absent in oil of its parent *M. arvensis*. Menthol is lower in 'Teton Mint' than in its parent and that of commercial *M. arvensis* and *M. piperita*. Organoleptically, the oil of 'Teton Mint' is different from that of 'Black Mitcham' and *M. arvensis*, reflecting the difference in oil component ratios.

TABLE 1

A Comparison of 'Teton Mint' Essential Oil collected from test plots near Monmouth, Oregon, to that of its *M. arvensis* parent, Commercial *M. arvensis*, and Commercial *M. piperita* Oils. 1/

| Essential Oil Components | 08-A20-4 Parent Seedling 2/ | Teton Mint Seedling 2/ | 'Blanco' Commercial *M. arvensis* | 'Black Mitcham' Commercial *M. piperita* |
|---|---|---|---|---|
| 1-Limonene | 4.8 | 1.9 | 1.4 | 1.7 |
| 1,8-Cineole | 0.0 | 1.1 | 0.0 | 4.9 |
| 1-Menthone | 55.4 | 61.7 | 21.5 | 19.4 |

TABLE 1-continued

A Comparison of 'Teton Mint' Essential Oil collected from test plots near Monmouth, Oregon, to that of its *M. arvensis* parent, Commercial *M. arvensis*, and Commercial *M. piperita* Oils. 1/

| Essential Oil Components | 08-A20-4 Parent Seedling 2/ | Teton Mint Seedling 2/ | 'Blanco' Commercial *M. arvensis* | 'Black Mitcham' Commercial *M. piperita* |
|---|---|---|---|---|
| Menthofuran | 0.0 | 1.4 | 0.0 | 4.2 |
| Isomenthone | 0.7 | 4.0 | 2.0 | 3.1 |
| 1-Menthyl Acetate | 3.1 | 1.2 | 3.7 | 5.3 |
| 1-Menthol | 23.3 | 8.0 | 67.7 | 44.6 |
| Pulegone | 0.0 | 0.6 | 0.0 | 2.1 |

The numbers listed in the above table are percentages based upon the analysis of the respective mint oils by gas chromatography. The percentages are determined by calculation of the relative peak areas.

1/ Commercial oils of *M. arvensis* ('Blanco') and *M. piperita* ('Black Mitcham') were samples of what is typically produced by mint growers.

2/ The essential oil of *M. arvensis* parent seedling (08-A20-4) and 'Teton Mint' were collected from plants growing in test plots in 2013 and 2014, respectively.

TAXONOMIC DESCRIPTION OF 'TETON MINT'

This new plant, under greenhouse and field growing conditions, is a bush type plant with lateral branches at each node of the main stems. The height of 'Teton Mint' is equal to or greater than Black Mitcham growing under similar conditions and will vary based on fertilizer, soil quality, and water application, amongst other known factors that affect growth patterns. Secondary and tertiary branching occurs to form a loose growth habit. When 'Teton Mint' is mature and ready for harvest, the main stem at mid-plant (approximately between the eleventh and twelfth node) is 3.1-3.4 mm in width. The secondary stem is 8.7-9.0 mm in width.

Mature leaves at the bottom of the plant are ovate lanceolate as are leaves on secondary branch stems. Leaves on upper mature plants, both main and secondary stems are more lanceolate (FIG. 1). Mid-main stem leaf size at flowering is 23-24 mm in width and 69-82 mm in length. Leaf size on secondary branches at flowering is 8.7-9 mm in width and 17-19 mm in length. Leaf petioles on the main stem leaves are 4.0-5.0 mm in length while petioles on secondary branch stem leaves are 5-6 mm in length. Leaves on the mid-main and lower stem tend to be slightly lobed and irregular denticulate. The main stem leaves have from 16-18 teeth on each side while the secondary branch leaves have 3-5 teeth on each side. The leaf is green in color, with The Fifth Edition Royal Horticultural Society Colour Chart of 144A in the yellow-green group classification. The leaf has 6-9 lateral veins, more or less in parallel off the main vein that runs from the petiole to the tip of the leaf. The veins are prominent in all leaves of 'Teton Mint'.

The inflorescence is a conspicuous spike with capitate flowers developing at the nodes of the spike stem. The cylindrical spikes are about 15 mm in diameter and range from 200 to 250 mm in length. The capitate flowers are 9-12 mm in width and 6-8 mm in length. The flowers consist of five petals fused into a two lipped corolla. The corolla is light violet in color as illustrated in The Fifth Edition Royal Horticultural Society Colour Chart 91D in the violet-blue group. The calyx is generally green and is 143C in The Fifth Edition Royal Horticultural Society Colour Chart, green group. The gynoecium consists of a single pistil with two lobed stigma that is exserted. The androecium consists of four stamens, each with a distinct filament and anther.

While the plant that comprises the present invention has been described in connection with a specific embodiment thereof, it will be understood that this application is intended to cover any variation, uses, or adaptation of the invention (particular those induced by cultivation under different environmental conditions) following, in general the principles of the invention and including such departures from the present disclosure as come within known or customary practice in the art to which the invention scope of the invention and the limits of the appended claim.

I claim:

1. A new and distinct variety of mint plant, substantially as shown and described, characterized particularly by improving resistance to mint wilt and producing a unique essential oil.

* * * * *